United States Patent
Machac, Jr. et al.

(10) Patent No.: US 6,515,145 B2
(45) Date of Patent: Feb. 4, 2003

(54) PROCESS FOR THE PRODUCTION OF CARBONATES THAT MELT AT A HIGH TEMPERATURE

(75) Inventors: James R. Machac, Jr., Lago Vista, TX (US); Edward T. Marquis, Austin, TX (US); Howard P. Klein, Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/752,118

(22) Filed: Dec. 29, 2000

(65) Prior Publication Data

US 2002/0087020 A1 Jul. 4, 2002

(51) Int. Cl.$^7$ .................. C07D 317/12; C07C 69/96
(52) U.S. Cl. ......................... 549/229; 558/260
(58) Field of Search .................. 558/260; 549/229, 549/230

(56) References Cited

U.S. PATENT DOCUMENTS

| | | | |
|---|---|---|---|
| 3,748,345 A | * 7/1973 | Pasquale et al. | 260/340.2 |
| 5,179,214 A | 1/1993 | Marquis et al. | 549/230 |
| 5,283,356 A | * 2/1994 | Marquis et al. | 558/260 |
| 5,733,860 A | * 3/1998 | Durbut et al. | 510/405 |
| 5,817,612 A | 10/1998 | Distaso | 510/203 |
| 5,821,209 A | 10/1998 | Distaso et al. | 510/207 |

OTHER PUBLICATIONS

Kihara, Nobuhiro, et al: "Synthesis and Properties of Poly-(hydroxyurethane)s" Journal of Polymer Science: Part A: Polymer Chemistry, vol. 31, 1993, pp. 2765–2773.

* cited by examiner

Primary Examiner—Cecilia Tsang
Assistant Examiner—Ebenezer Sackey
(74) Attorney, Agent, or Firm—Gardere Wynne Sewell LLP

(57) ABSTRACT

A method for preparing carbonates includes reacting an alkylene oxide with carbon dioxide in the presence of a catalyst and a non-protic solvent. The method further includes having the boiling point of the solvent greater than about 70 ° C., and removing the solvent from the reaction product. The solvent used in the various forms of the present invention can be glyme, diglyme, tetraglyme, cumene, toluene, tetrahydofuran, cyclohexanone, ethylbenzene, aromatic hydrocarbons, or ethers. The catalyst used can be a tetraalkyl ammonium halide, such as tetraethyl ammonium bromide. The alkylene oxide that can be used in the invention can include Bisphenol A, Bisphenol B, Bisphenol F, alkylene oxides that have alkyl substituent groups, alkylene oxides that have aryl substituent groups, and alkylene oxides that contain both alkyl and aryl substituent groups. An essentially solvent free carbonate can be prepared by flash removal of the solvent.

27 Claims, No Drawings

PROCESS FOR THE PRODUCTION OF CARBONATES THAT MELT AT A HIGH TEMPERATURE

TECHNICAL FIELD

The present invention relates in general to the field of organic synthesis, and more particularly to a method for producing organic carbonates.

BACKGROUND OF THE INVENTION

Alkylene carbonates are valuable compounds that are useful in a variety of applications, either directly, or as reactive intermediates. Examples of such applications include uses as cleaning and stripping agents, monomers for making polycarbonate plastics, alkoxylating agents for use in producing reactive intermediates, incorporation into plant protection agents and pharmaceuticals, and the synthesis of carbamates.

It is known that alkylene oxides will react with carbon dioxide and a suitable catalyst to produce organic carbonates. However, to achieve industrially acceptable reaction rates, high temperatures and pressures are often used. Such conditions are expensive to maintain and often result in decomposition of the carbonate precursors.

Additional problems are encountered when higher molecular weight alkylene oxides are used. The carbonates produced from these alkylene oxides are typically solids at room temperature, and viscous liquids under reactor conditions. The increase in viscosity as the reaction proceeds inhibits effective mixing and carbon dioxide uptake, and thus lowers the yield. The product, containing unreacted starting material, must then be removed from the reactor while very hot to avoid the problems associated with solidification of the product mixture.

There exists a need for a method for the production of carbonates that melt at a high temperature, which process both increases the yield of the product, and facilitates the handling of the product once it is produced.

SUMMARY OF THE INVENTION

The present invention solves the problems of reduced yields and difficulty in manipulating higher-melting organic carbonates.

The present invention is a method for the production of organic carbonates by reacting an alkylene oxide and carbon dioxide in the presence of a catalyst and a solvent. The solvent used in the various forms of the present invention can be glyme, diglyme, tetraglyme, cumene, toluene, tetrahydofuran, cyclohexanone, ethylbenzene, aromatic hydrocarbons, or ethers. The catalyst used can be a tetraalkyl ammonium halide, such as tetraethyl ammonium bromide. The alkylene oxide that can be used in the invention can include Bisphenol A, Bisphenol B, Bisphenol F, alkylene oxides that have alkyl substituent groups, alkylene oxides that have aryl substituent groups, and alkylene oxides that contain both alkyl and aryl substituent groups.

An advantage of the present invention is that the claimed method results in near quantitative (that is, almost 100%) conversion of starting materials into carbonate product. Additionally, the presence of the essentially pure carbonate in a solvent matrix facilitates the collection and distribution of the material for further use. An essentially solvent-free carbonate can be prepared by flash removal of the solvent.

DETAILED DESCRIPTION OF THE INVENTION

The compositions of the present invention contain a wide variety of other organic solvents. Non-limiting examples of representative classes of such solvents include hydrocarbons, ethers, esters, sulfur-based solvents, chlorinated hydrocarbons, aromatic hydrocarbons nitrated hydrocarbons, amides, and ketones. Such solvents may be polar or non-polar, may be protic or aprotic, may be cyclic, branched, or straight chain, and may contain one or more functional groups.

While a wide variety of organic solvents can be used in the compositions of the present invention, some solvents that might be predicted to work do not. For example, propylene carbonate produces low yields of carbonates under the same conditions that lead to quantitative conversion using other solvents.

Representative examples of common hydrocarbon solvents appropriate for use in the present invention include, but are not limited to, toluene, xylene, and mixtures of aromatic hydrocarbons.

Examples of common ether solvents that may be used in the present invention include, but are not limited to, tetrahydrofuran, dioxane, glyme, diglyme, tetraglyme, dibutyl ether, and diphenyl ether.

Examples of common sulfur-based solvents that can be used in the present invention include, but are not limited to, dimethylsulfoxide (DMSO) and sulfolane.

Representative examples of common chlorinated hydrocarbon solvents include, but are not limited to, methylene chloride, methyl chloroform, chlorobenzenes and dichlorobenzenes.

Representative examples of common amide solvents include, but are not limited to, formamide, dimethyl formamide, acetamide, and dimethylacetamide.

Representative examples of common ketone solvents include, but are not limited to, acetone, methyl ethyl ketone (MEK), methyl isobutyl ketone, methyl isoamylketone, and cyclohexanone.

The conditions under which the present invention may be practiced vary. Typically, the process will be conducted under elevated temperatures. The following examples are illustrative of this invention, and are not intended to limit the scope of the claimed subject matter of the present invention.

EXAMPLE 1

Carbonation of Bisphenol A

Bisphenol A (4428 g, 24.6 mols of epoxide groups) in the form of an epoxy resin (EPON 828) was placed in a 3-gallon stainless steel autoclave reaction vessel along with diglyme (2805.2 g) and tetraethyl ammonium bromide (30.3 g). The autoclave was flushed with nitrogen and pressurized with carbon dioxide (1320 g, 30.0 mols). The autoclave was then heated to 170° C. The reaction mixture was maintained at 170° C. with stirring until the uptake of carbon dioxide had ceased. The reactor was allowed to cool until the temperature was between 80° C. and 90° C. The reaction mixture was then poured from the autoclave to yield 8179.4 g of Bisphenol A carbonate and diglyme solvent.

Analysis of the material from the reactor by $^{13}C$ Nuclear Magnetic Resonance spectroscopy showed that it contained only the carbonate of Bisphenol A, diglyme solvent and very small amounts of unidentified compounds. There were no significant amounts of side products, and no unreacted Bisphenol A diglycidyl ether (EPON 828).

EXAMPLE 2

Flash Solvent Removal

The diglyme solvent was removed from the product by the application of heat and reduced pressure. A 200 g sample of Bisphenol A carbonate reaction product from Example 1 was placed in a flask and heated to 135° C. under vacuum. The flask was then allowed to cool, while maintaining the vacuum. The resulting Bisphenol A carbonate contained approximately 2% diglyme solvent. The process removed 78.3 grams of diglyme.

EXAMPLE 3

Carbonation of Bisphenol F

Bisphenol F (4230 g, 24.6 mols of epoxide) in the form of an epoxy resin (DER 354 and EPON 862) was placed in a 3-gallon stainless steel autoclave reaction vessel along with diglyme (2811 g) and tetraethyl ammonium bromide (30 g). The autoclave was flushed with nitrogen and pressurized with carbon dioxide (1320 g, 30.0 mols). The autoclave was then heated to 170° C. The reaction mixture was maintained at 170° C. with stirring until the uptake of carbon dioxide had ceased. The reactor was allowed to cool until the temperature was between 80° C. and 90° C. The reaction mixture was then poured from the autoclave to yield 8179.4 g of Bisphenol F carbonate and diglyme solvent.

Analysis of the material from the reactor by $_{13}C$ Nuclear Magnetic Resonance spectroscopy showed that it contained only the carbonate of Bisphenol F, diglyme solvent and very small amounts of unidentified compounds. There were no significant amounts of side products, and no unreacted Bisphenol F diglycidyl ether (DER-354 and EPON 862).

COMPARATIVE EXAMPLE 1

Attempted Carbonation of Bisphenol A Without Solvent

Bisphenol A (170 g, about 1.0 mole of epoxide) in the form of an epoxy resin (EPON 828) was placed in a 3-gallon stainless steel autoclave reaction vessel along with tetraethyl ammonium bromide (12.05 g). The autoclave was flushed with nitrogen and pressurized with carbon dioxide (625 g, 14.2 mols). The autoclave was then heated to 180° C. The reaction mixture was maintained at 180° C. with stirring until the uptake of carbon dioxide had ceased. The consumption of carbon dioxide was 1.68 mmol $CO_2$ per gram of epoxy resin. The amount of carbon dioxide that would have been consumed for the total conversion to the carbonate would have been 4.67 mmol $CO_2$ per gram of epoxy resin. Therefore, the conversion was far from complete. The reactor was allowed to cool to 140° C. and a vacuum was applied for two hours to degas the reaction product mixture. The reaction product mixture was then poured from the autoclave. The product of the reaction was a mixture of the carbonate of Bisphenol A and unreacted Bisphenol A.

COMPARATIVE EXAMPLE 2

Attempted Carbonation of Bisphenol A Using Propylene Carbonate Solvent.

Bisphenol A (342 g, about 2.0 mols of epoxide) were reacted with carbon. dioxide (132 g, 3 mols), tetraethyl ammonium bromide (5 g) and propylene carbonate (102.1 g) in a stainless steel autoclave at 180° C. for two hours. The reaction had essentially ceased at that point as indicated by the decrease in the uptake of carbon dioxide. The amount of carbon dioxide consumed per gram of Bisphenol A was 2.87 while the theoretical amount was calculated as 4.03 mmol of carbon dioxide per gram of Bisphenol A. This indicates that the reaction ceased long before the complete conversion of the starting material into the carbonate of Bisphenol A. The reaction product was a viscous liquid at room temperature.

What is claimed is:

1. A method for preparing carbonates comprising:
   reacting an alkylene oxide with carbon dioxide in the presence of a catalyst and a non-protic solvent.
2. The method recited in claim 1, wherein the boiling point of the solvent is greater than about 70° C.
3. The method recited in claim 1 further comprising the removal of the solvent from the reaction product.
4. The method recited in claim 1 wherein the solvent comprises glyme.
5. The method recited in claim 1 wherein the solvent comprises diglyme.
6. The method recited in claim 1 wherein the solvent comprises triglyme.
7. The method recited in claim 1 wherein the solvent comprises tetraglyme.
8. The method recited in claim 1 wherein the solvent comprises cumene.
9. The method recited in claim 1 wherein the solvent comprises toluene.
10. The method recited in claim 1 wherein the solvent comprises tetrahydrofuran.
11. The method recited in claim 1 wherein the solvent comprises cyclohexanaone.
12. The method recited in claim 1 wherein the solvent comprises ethylbenzene.
13. The method recited in claim 1 wherein the solvent comprises an aromatic hydrocarbon.
14. The method recited in claim 1 wherein the solvent comprises an ether.
15. The method recited in claim 1, wherein the alkylene oxide comprises Bisphenol A.
16. The method recited in claim 1, wherein the alkylene oxide comprises Bisphenol B.
17. The method recited in claim 1, wherein the alkylene oxide comprises Bisphenol F.
18. The method recited in claim 1, wherein the alkylene oxide contains an alkyl substituent group.
19. The method recited in claim 1, wherein the alkylene oxide contains an aryl substituent group.
20. The method recited in claim 1, wherein the alkylene oxide contains both an alkyl and an aryl substituent group.
21. The method recited in claim 1, wherein the alkylene oxide is in the form of an epoxy resin.
22. The method recited in claim 1, wherein the alkylene oxide comprises a solid at room temperature.
23. The method recited in claim 1, wherein the alkylene oxide is a viscous liquid at room temperature.
24. The method recited in claim 1, wherein the reaction is conducted between about 170° C. and 190° C.
25. The method recited in claim 1 wherein the catalyst comprises a tetraalkylammonium halide.
26. The method recited in claim 1 wherein the catalyst comprises tetraethylammonium bromide.
27. The composition produced by the method recited in claim 1.

* * * * *